United States Patent [19]

Weekley

[11] Patent Number: 5,624,412
[45] Date of Patent: Apr. 29, 1997

[54] I-V CADDY

[76] Inventor: Jack L. Weekley, 3358 S. Old State Rd. 15, Wabash, Ind. 46992

[21] Appl. No.: 500,824

[22] Filed: Jul. 11, 1995

[51] Int. Cl.$^6$ .................................................. A61M 25/00
[52] U.S. Cl. ........................... 604/280; 604/263; 206/366; 206/370
[58] Field of Search ........................................ 604/181, 187, 604/192, 263, 280; 206/363–370, 443, 438; 211/60.1, 69, 70.1, 71–73

[56] References Cited

U.S. PATENT DOCUMENTS

| 4,844,249 | 7/1989 | Coulombe | 206/438 |
|---|---|---|---|
| 4,890,734 | 1/1990 | Gach | 206/366 |
| 5,099,992 | 3/1992 | Heimreid | 206/366 |
| 5,160,324 | 11/1992 | Halbach | 604/192 |
| 5,190,169 | 3/1993 | Sincock | 211/60.1 |
| 5,435,448 | 7/1995 | Kempen | 206/370 |
| 5,469,964 | 11/1995 | Bailey | 206/364 |

Primary Examiner—Corrine M. McDermott
Attorney, Agent, or Firm—Liell & McNeil

[57] ABSTRACT

The I-V Caddy of the present invention is designed to provide a safe and convenient holder for needles, syringes, I-V tubing and its accompanying injection ports in the area adjacent where a health care provider is providing medical treatment to a patient. The I-V Caddy of the present invention helps to avoid potentially dangerous needle sticks by allowing health care providers to uncap, use and recap needles and syringes in a safe one-handed fashion. The I-V Caddy preferably includes a stainless steel platform body which includes a plurality of various size openings therethrough that are sized to receive a needle or syringe cap. The needle caps are held in place on the platform body utilizing either threaded openings or a spring loaded gripping device. Also attached to the platform body is at least one I-V port device holder that permits such a port device to be held firmly in place on the platform body so that the health care provider can inject fluids into the I-V tubing without having their free hand in a position where an accidental needle stick might occur.

8 Claims, 5 Drawing Sheets

I-V CADDY

FIELD OF THE INVENTION

This invention relates generally to a device for holding medical related implements during a medical procedure, and more particularly to an I-V Caddy capable of holding needles, syringes, I-V tubing, stopcocks and I-V ports, etc., in the immediate vicinity of a patient undergoing medical treatment.

BACKGROUND OF THE INVENTION

In many medical treatment situations, an anesthesiologist or other physician often needs to have a number of medications prepared for injection into the patient, and the patient often has at least one I-V tube entering their body. The I-V tubing typically includes a number of ports and stopcocks located on one or more branches of the I-V tubing in order to facilitate the delivery of medications to the patient. Generally, the past practice is to tape the various injection ports onto sheets of an operating table or allow the I-V tubing and injection ports and stopcocks to dangle. This is very undesirable since the health care provider must often hold the stopcock or injection port while pushing the needle of a syringe therein. This two handed procedure runs the obvious risk of potential needle sticks. Apart from the handling problems, there is also the problem of storing the prepared syringes in a safe manner but in a convenient location for their later use during the medical procedure. In other words, it is desirable that the prepared syringes be immediately accessible in the area of where the medical treatment is being performed, but be stored in a way that it eliminates the risk of accidental needle sticks. Furthermore, a problem often encountered is what to do with spent syringes that tend to litter an operating area. Each of these spent syringes poses the threat of an accidental needle stick, which could expose the health care provider to potentially deadly infectious diseases such as AIDS or Hepatitis. The present invention is directed to overcoming these and other problems associated with convenience and safety in handling I-V tubing related items and syringes.

SUMMARY OF THE INVENTION

The present invention is a holding device for use in an operating room to safely hold I-V tubing with attached injection ports, stopcocks, and also to hold prepared and used syringes. The I-V Caddy of the present invention includes a support bracket which may appear either in the form of a clamp that attaches to an I-V pole or an elongated support portion that can extend under the pillow of a patient in order to provide stability if no support pole is available or convenient for a particular situation. A platform body includes a base portion that mates to the support bracket. The platform body includes a first portion with a plurality of openings therethrough that are arranged in a pattern and sized to receive a needle or syringe cap (hereinafter needle cap). The platform body also includes a second portion with a surface. Also included are means, attached to the platform body, for removably holding needle caps received in one of the plurality of openings. Finally, the I-V Caddy includes means, attached to the platform body, for removably holding an I-V port device (i.e. I-V tubing with side ports and/or stopcocks) against said surface in a substantially fixed position relative to the platform body.

One object of the present invention is to aid health care providers in safely and conveniently handling needles and I-V port devices in the vicinity of a patient.

Another object of the present invention is to provide a safe one handed method of recapping spent needles.

Still another object of the present invention is to provide an improved I-V Caddy for holding needles, syringes, and I-V port devices, such as stopcocks and injection ports.

DETAILED DESCRIPTION OF THE PREFERRED EMBODIMENT

Figure 1:
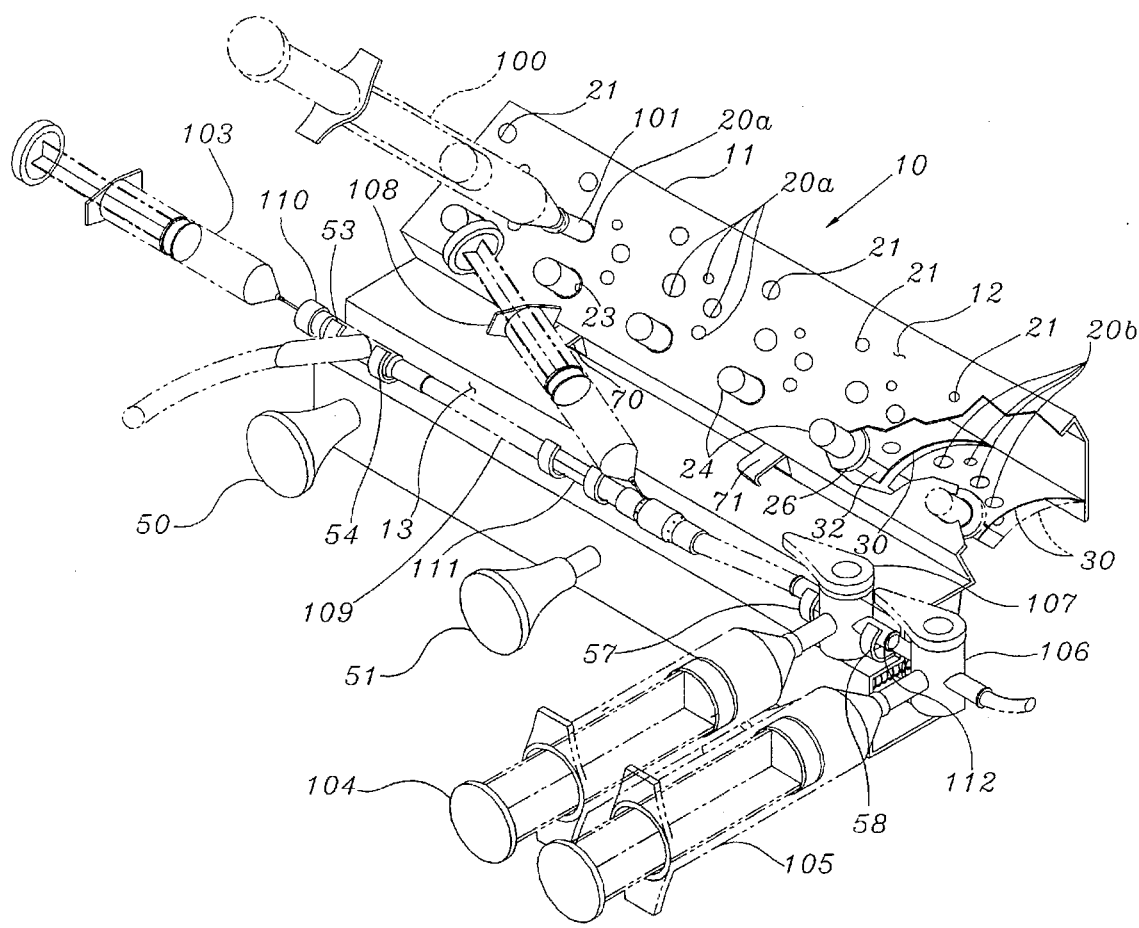
FIG. 1 is an isometric view of an I-V Caddy according to the preferred embodiment of the present invention holding an I-V port device and a prepared syringe in accordance with the present invention.
Figure 2:
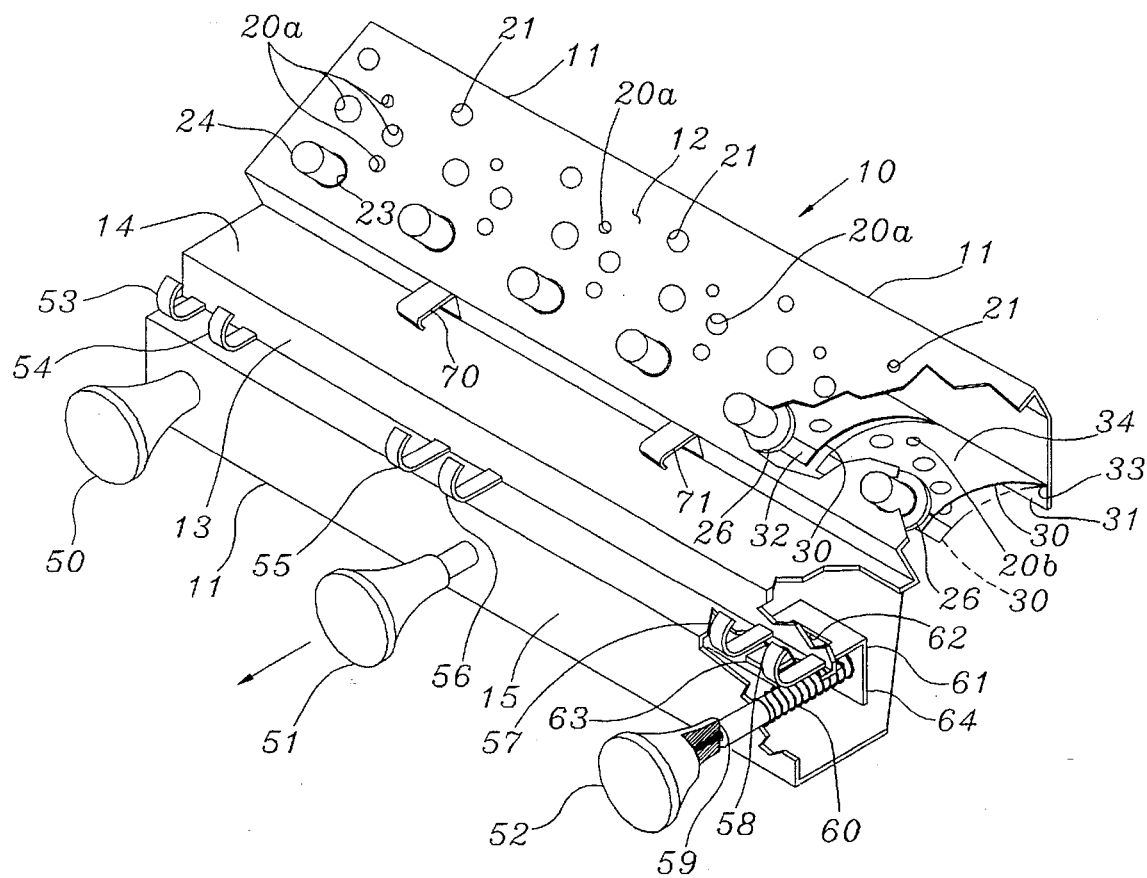
FIG. 2 is a partially fragmented isometric view of an I-V Caddy according to the preferred embodiment of the present invention.
Figure 3:
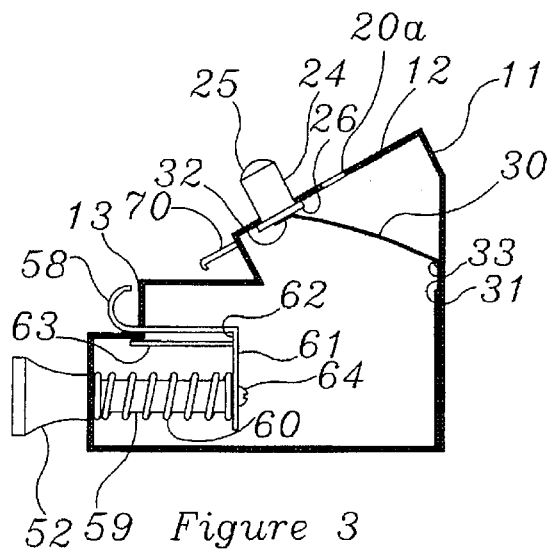
FIGS. 3–5 are a series of side elevational views of an I-V Caddy according to the present invention illustrating the holding action of the present invention.

Referring now to FIG. 1, an I-V Caddy 10 according to the present invention is shown in one possible configuration during a medical procedure. I-V Caddy 10 is primarily built around a platform body 11, which is preferably formed from a single sheet of stainless steel for easy cleaning and durability. In particular, the stainless steel sheet is formed to include a first surface portion 12 having a plurality of openings 20a, 21 and 23 therethrough that are arranged in a pattern. The first set of openings 21, which extend adjacent the top edge of first surface portion 12, are threaded and sized to receive a variety of different sized needle caps. Threaded openings 21 can be utilized to hold a needle cap by simply inserting the unused syringe or needle with its cap through the opening 21 and then twisting the same in order to engage the threads. The syringe or needle can then remain safely in that position attached to platform body 11 until use.

As better illustrated in FIGS. 2–5, a second set of openings 20a through first surface portion 12 are in a variety of sizes and are arranged in a pattern. The various sizes are intended to accommodate the wide variety of diameters in which needle or syringe caps are manufactured. Unlike threaded openings 21, openings 20a utilize a different method of holding the needle or syringe cap. A plurality of cap holders 30 are attached to platform body 11 underneath first surface portion 12.

Cap holders 30 are preferably cut from a piece of spring stainless steel sheet and formed to include a holding portion 34 separated from a base portion 31 by an elastically deformable bend 33 that functions as a biased hinge. The holding portion 34 of each cap holder 30 includes a plurality of openings 20b are arranged and sized in a pattern to correspond to the pattern of openings 20a in first surface portion 12. Cap holders 30 are preferably welded along base portion 31 to platform body 11 and include a free end 32 that is biased toward the underside of first surface portion 12 by the spring action of elastically deformable bend 33. A plurality of needle releases 24 include a cylindrical button portion 25 that extends above first surface portion 12 through openings 23. Needle releases 25 also include a flanged end 26 which rests against the free end 32 of cap holder 30. The spring action of bend 33 causes cap holder 30 toward a gripping position (see FIGS. 3 and 5); however, cap holder 30 can be moved to a release position (see FIG. 4) when the button 25 of needle release 24 is depressed downward toward first surface portion 12 of platform body 11.

Figure 4:
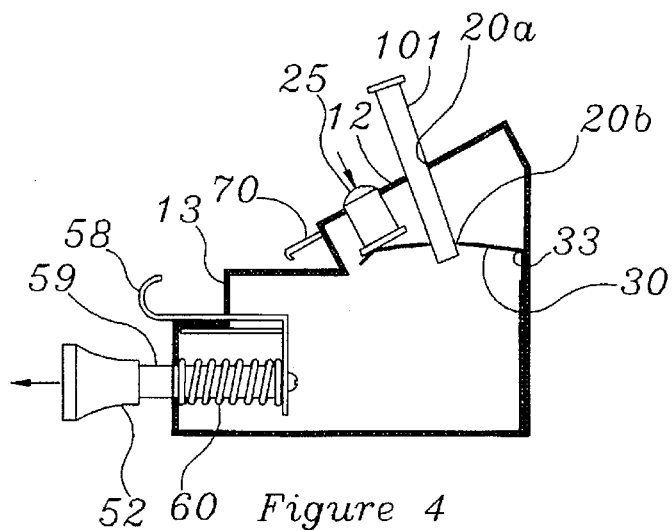
Figure 5:
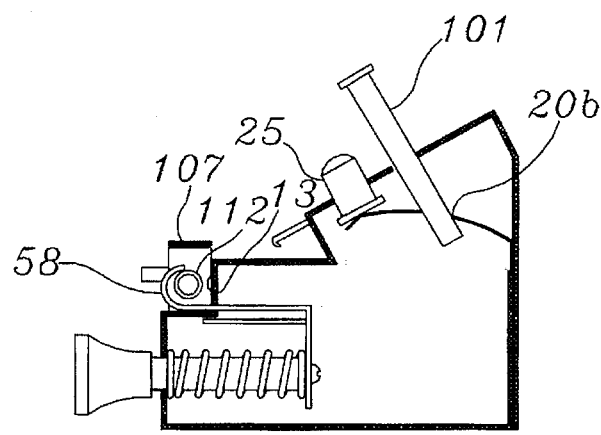

When in the release position as shown in FIG. 4, clearance holes 20b become aligned with their corresponding openings 20a to allow a needle cap 101 to be inserted easily through an opening 20a and a corresponding opening 20b in cap holder 30. Next, when button surface 25 is released, the spring action of elastically deformable bend 33 causes the needle cap 101 to become wedged in the clearance hole 20b. When in this gripping position, needle cap 101 cannot be removed from platform body 11 until the needle release 24 is again depressed toward its release position.

Thus, threaded openings 21 as well as the interaction of cap holders 30 with openings 20a constitute a means for removably holding a needle cap on platform body 11. Although not shown, the present invention could be easily modified to accommodate so called "needless syringes" and in some situations it may be desirable to include a cap stop plate underneath cap holders 30 in order to limit how far a needle cap can be advanced through clearance holes 20b in cap holders 30.

When in use, platform body 11 can be pre-loaded with a variety of needles and syringes holding different medications that the physician or other health care provider anticipates using during a particular medical treatment. The platform body with the needle and/or syringes is mounted adjacent the medical treatment area for convenient and easy access by the health care provider. When it becomes time to use the particular syringe, the health care provider simply grasps that particular syringe with one hand and withdraws it from its cap which is kept held by I-V Caddy 10. After injecting the medication, the health care provider simply re-inserts the needle or syringe into its cap with a simple and safe one handed procedure that avoids the possibility of needle sticks which could otherwise occur when one attempts to recap a needle using two hands. The present invention also saves time during medical treatment procedures by allowing the health care provider to simply return the spent needle to I-V Caddy 10 instead of being required to walk across a room and dispose of the needle or syringe in a biohazard sharps container. When using the present invention, the complete platform body 11 is moved to the sharps container after the medical procedure and the spent needle and syringes are removed from platform body 11 and disposed of properly.

In addition to the present invention's ability to safely and conveniently hold needles and syringes during a medical procedure, the invention also provides means, attached to platform body 11, for removably holding I-V port devices against surface 13 in a substantially fixed position relative to the platform body. (See FIG. 1). As used in this document, the term I-V port device refers to any collection or configuration of I-V tubing having injection ports, stopcocks and other various components known in the art, such as regulating clamps, etc.

Referring again to FIGS. 2–5, I-V Caddy 10 includes a plurality of port holders 61 spring mounted to platform body 11 adjacent surface 13. Port holders 61 are preferably shaped from a single piece of sheet metal to include a guide portion 63, a stop 62, a base portion 64 and a pair of hook portions, such as hook portions 57 and 58. The various hook portions 53–58 of port holders 61 extend through rectangular openings in surface 13. In order to actuate port holders 61, a plurality of holder releases 50–52 are provided to include a stem extending through surface 15 of platform body 11. A knob is attached to one end of each stem 59 and the other end of the stems are attached to base portion 64 of cap holder 61. A compression spring 60 is mounting about each stem 59 in order to bias cap holders 61 in the direction of pulling hook portions 53–58 inward toward surface 13 into a holding position. However, hook portions 53–58 can be retracted away from surface 13 to a loading position (FIG. 4) against the action of compression spring 60 simply by pulling outward on the knobs of holder releases 50–52. When in a loading position, a portion of I-V tubing, a syringe port or even a stopcock and most other I-V port devices can be positioned to be straddled by the hook portions 53–58. When the holder releases 50–52 are released to retract under the action of springs 60, the I-V port device is held firmly in place against surface 13.

This configuration allows the health care provider to avoid allowing the I-V port device to dangle near the patient, which often makes it difficult to inject medications into the I-V tubing without the risk of an accidental needle stick. When using the present device, the injection port or other I-V port device is held firmly on platform body 11 and allows the health care provider to have their free hand clear of the I-V port device when the syringe or needle is inserted therein.

Figure 6:
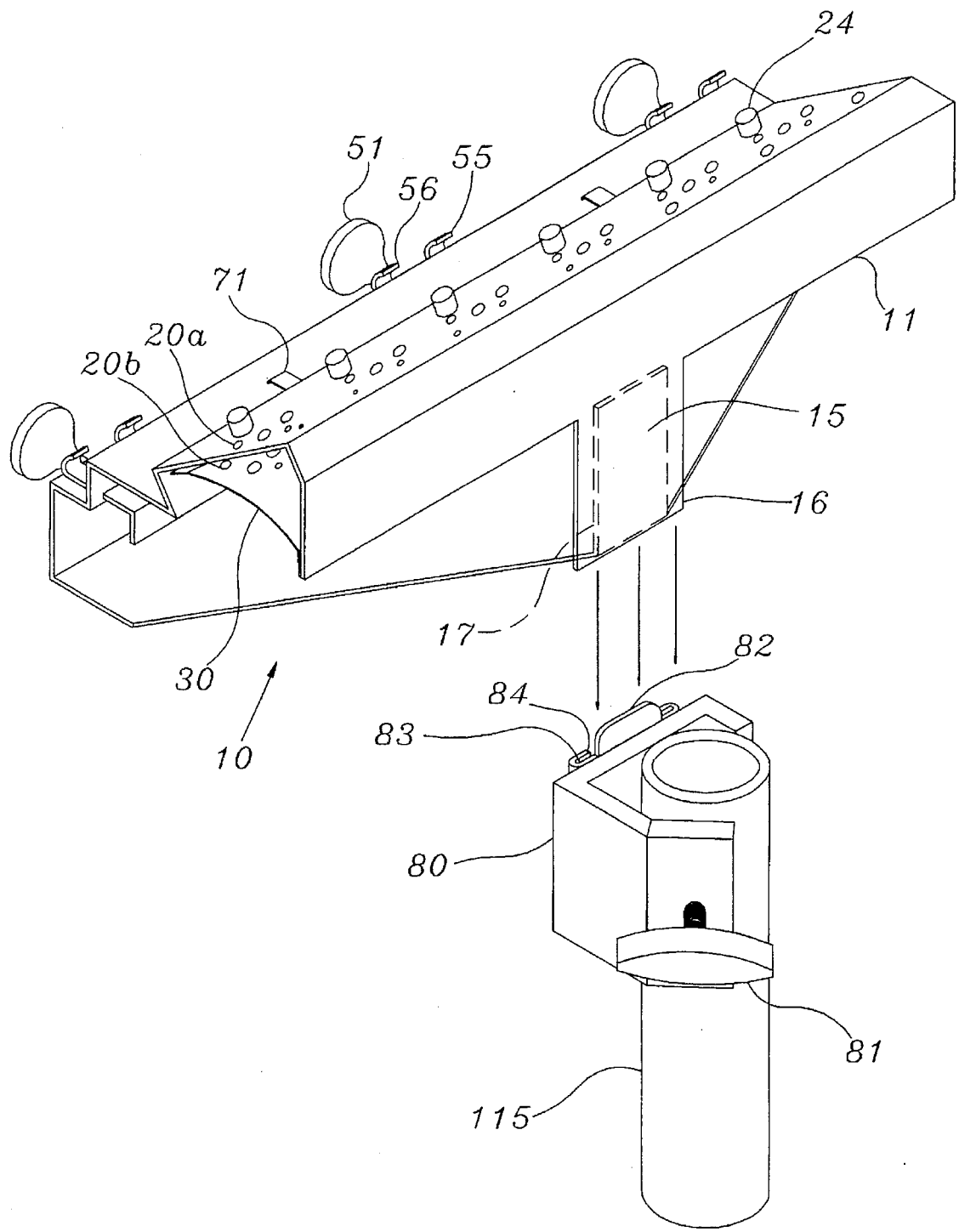
FIG. 6 is a rear isometrical view of an I-V Caddy according to the present invention before being mated to a support bracket according to one aspect of the present invention.
Figure 7:
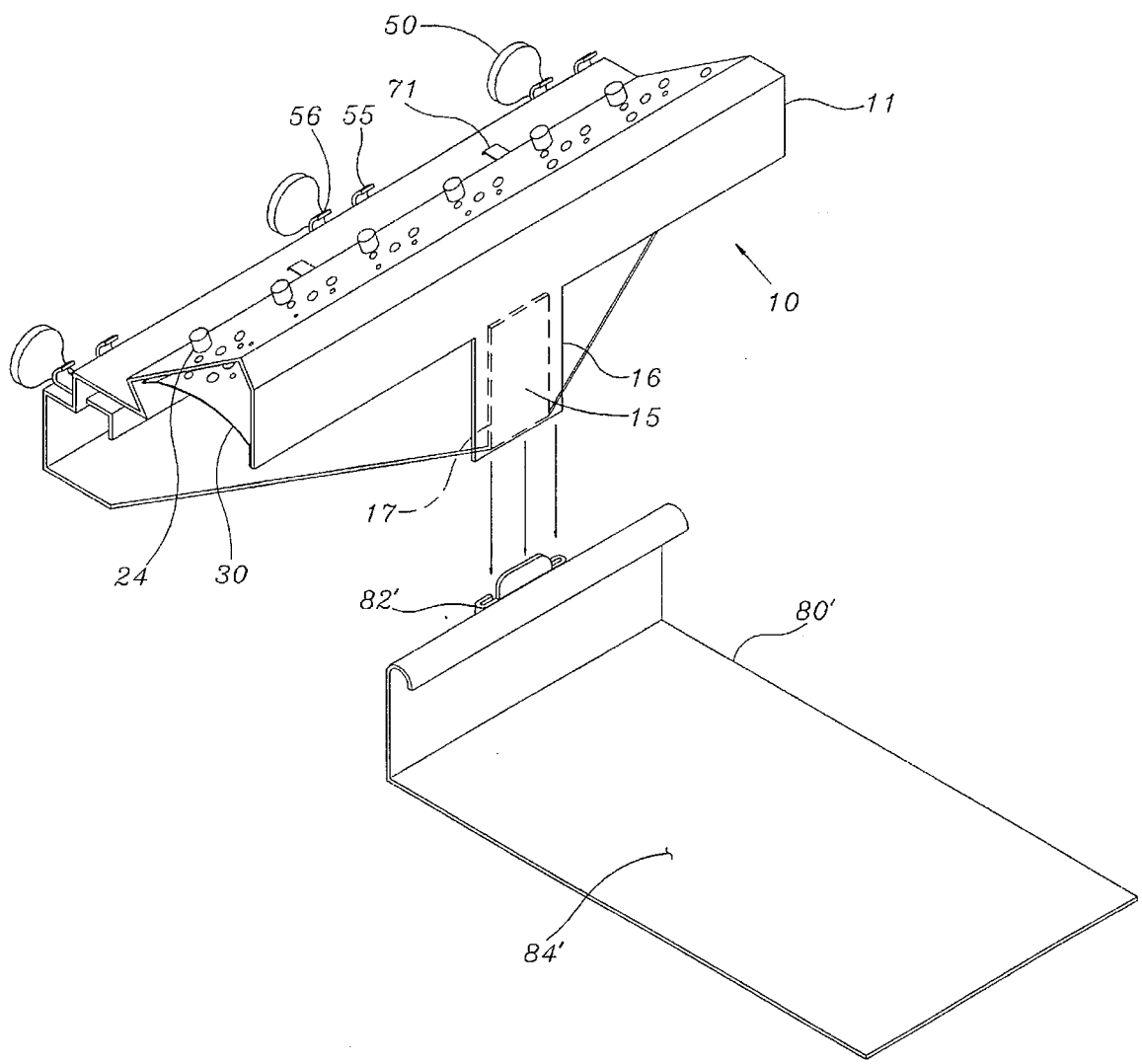
FIG. 7 is a rear isometrical view of an I-V Caddy according to the present invention before being mated to a support bracket according to another aspect of the present invention.

Referring now to FIGS. 6 and 7, the other features of the present invention which facilitate mounting the platform body 11 adjacent a medical treatment area are illustrated. As stated earlier, platform body 11 is preferably formed from a single sheet of stainless steel sheet metal, and includes tabs 16 and 17 formed on each end of the piece of sheet metal. When formed, tabs 16 and 17 preferably lay against one another and are spot welded together in area 15 as shown in FIG. 6. Tabs 16 and 17 are shaped and sized to be received in respective channels 83 and 84 of support bracket 82. In other words, the width of tab 16 is just smaller than the width of channel 83 and the width of channel 84 is just larger than the width of tab 17. Thus, platform body 11 mates to support bracket 82 and is held firmly in place. Attached to support bracket 82 is a clamp 80 which is sized to mount around a typical I-V pole 115 or other similar structure. Clamp 80 is secured to the I-V pole 115 by a winged set-screw 81. Thus, when in use, one or more I-V Caddys 10 according to the present invention can be mounted on I-V poles adjacent a medical treatment area in order to organize the various I-V port devices and provide a safe and convenient method of storing needles and syringes before and after their use.

FIG. 7 shows an alternative method of supporting platform body 11 which utilizes a support bracket 82' attached to an L-shaped piece of sheet metal 80' that includes an elongated portion 84' which could be received underneath the pillow of a patient undergoing medical treatment. This allows I-V Caddy 10 to be positioned adjacent the patient's pillow in the medical treatment area.

It should be understood that the above described embodiment is intended for illustrative purposes only in that those skilled in the art can appreciate that the concepts and teachings of the present invention can take a wide variety of forms. For instance, platform body 11 can be formed into a variety of different shapes without departing from the scope of the present invention, and shapes other than hook portions 53–58 could satisfactorily hold the various I-V port devices.

In any event, the scope of the present invention is defined by the claims as set forth below.

I claim :

1. An I-V Caddy comprising:

a support bracket;

a platform body having a first portion with a plurality of openings therethrough that are arranged in a pattern and sized to receive a needle cap, attached to a second portion with a surface having an opening therein and attached to a base portion that mates to said support bracket;

means, attached to said platform body, for removably holding a needle cap received in one of said plurality of openings;

means, attached to said platform body, for removably holding an I-V port device against said surface in a substantially fixed position relative to said platform body;

wherein said means for removably holding a needle cap includes a portion of said plurality of openings having threads capable of engaging a needle cap;

wherein said means for removably holding a needle cap further includes at least one cap holder having a base part attached to said platform body, a free end and a plurality of clearance holes therethrough that are arranged in a second pattern and sized to receive a needle cap;

said base part including a biased hinge portion that biases said free end toward a gripping position in which a needle cap is wedged in one of said clearance holes, but said free end being movable to a release position against the action of said biased hinge portion a sufficient distance that a needle cap becomes unwedged in said one of said clearance holes; and at least one needle release mounted on said platform and being in contact with one of said at least one cap holder and being capable of moving said free end to said release position.

2. The I-V Caddy of claim 1, wherein said cap holders is a piece of sheet metal and said biased hinge portion is an elastically deformable bend;

said at least one needle release has a flanged end in contact with said free end of one of said cap holders and a cylindrical button portion that extends through and one said first portion of said platform body.

3. The I-V Caddy of claim 2, wherein said means for removably holding an I-V port device includes at least one port holder mounted on said platform adjacent said surface and having a first hook portion and a second hook portion, said first hook portion and said second hook portion being parallel, said port holder being movable between a holding position in which said hook portions are close to said surface and a loading position in which said hook portions are away from said surface;

means for biasing said at least one port holder toward said holding position; and at least one holder release mounted on said platform and being in contact with one of said at least one port holders and being capable of moving said one of said at least one port holders toward said loading position against the action of said biasing means.

4. The I-V Caddy of claim 3, wherein said port holder is formed from a single piece of sheet metal to include a guide portion, a stop, a base and said hook portions all integrally attached to one another;

said at least one holder release including a stem extending through said opening in said surface and having a knob attached to one end and said base of said port holder on its other end; and said biasing means includes a compression spring mounted about said stem and compressed between said platform body and said base portion of said port holder.

5. The I-V Caddy of claim 4, wherein said platform body includes a second piece of sheet metal having a plurality of bends; and each of said first portion, said second portion and said base portion being apart of said second piece of sheet between two of said plurality of bends.

6. The I-V Caddy of claim 5, wherein said second piece of sheet metal has opposite ends attached together to form said base portion of said platform body.

7. The I-V Caddy of claim 6, wherein said support bracket includes a clamp attached thereto which is removably attachable to a support pole.

8. The I-V Caddy of claim 6, wherein said support bracket includes a horizontal mounting plate attached thereto of sufficient size to extend under a significant portion of a pillow.

* * * * *